United States Patent [19]

Kleemann et al.

[11] 4,175,088
[45] Nov. 20, 1979

[54] PROCESS FOR THE PRODUCTION OF [1,1-DITHIENYL-(3)-1-HYDROXYPROPYL-(3)]-[1-PHENYL-1-HYDROXYPROPYL-(2)]-AMINE AND [1,1-DITHIENYL-(3)-PROPEN-(1)-YL-(3)]-[1-PHENYLPROPYL-(2)]-AMINE

[75] Inventors: Axel Kleemann; Reinhold Kiel, both of Hanau; Ingomar Nubert, Offenbach, all of Fed. Rep. of Germany

[73] Assignee: Deutsche Gold- und Silber-Scheideanstalt vormals Roessler, Frankfurt, Fed. Rep. of Germany

[21] Appl. No.: 867,294

[22] Filed: Jan. 5, 1978

[30] Foreign Application Priority Data

Jan. 12, 1977 [GB] United Kingdom ............... 1120/77

[51] Int. Cl.$^2$ .................................... C07D 333/16
[52] U.S. Cl. ............................................ 549/59
[58] Field of Search ............................. 260/332.3

[56] References Cited

U.S. PATENT DOCUMENTS

| 3,251,858 | 5/1966 | Thiele et al. | 260/332.3 |
| 3,766,173 | 10/1973 | Thiele et al. | 260/240 R |

FOREIGN PATENT DOCUMENTS 1921453  9/1972  Fed. Rep. of Germany ........ 260/332.3

OTHER PUBLICATIONS

Morrison & Boyd, "Organic Chemistry", pp. 91–92, 456–457, 676, 683, 742, 840–841.

*Primary Examiner*—Gerald A. Schwartz
*Attorney, Agent, or Firm*—Cushman, Darby & Cushman

[57] ABSTRACT

[1,1-dithien-(3)-yl-1-hydroxy-(3)-propyl]-[1-phenyl-1-hydroxy-(2)-propyl]-amine is prepared by condensing thien-(3)-yl lithium with a β-halogen propionic acid alkyl ester of the formula

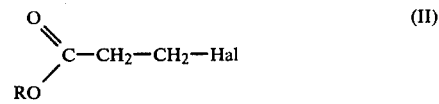

where R is a lower alkyl group and Hal is chlorine, bromine or iodine, in an inert medium at a temperature below −50° C. to form a compound of the formula

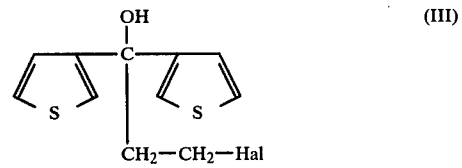

which is then reacted with 2-amino-1-hydroxy-1-phenylpropane in an inert medium in the presence of a basic compound. The product cn be converted to [1,1-dithien-(3)-yl-(1)-propen-(3)-yl]-[1-phenyl-(2)-propyl]-amine by dehydration.

8 Claims, No Drawings

PROCESS FOR THE PRODUCTION OF [1,1-DITHIENYL-(3)-1-HYDROXYPROPYL-(3)]-[1-PHENYL-1-HYDROXYPROPYL-(2)]-AMINE AND [1,1-DITHIENYL-(3)-PROPEN-(1)-YL-(3)]-[1-PHENYLPROPYL-(2)]-AMINE

BACKGROUND OF THE INVENTION

This invention relates to a process for the production of [1,1-dithien-(3)-yl-1-hydroxy-(3)-propyl]-[1-phenyl-1-hydroxy-(2)-propyl]-amine and [1,1-dithien-(3)-yl-(1)-propen-(3)-yl]-[1-phenyl-(2)-propyl]-amine.

It is known that [1,1-dithien-(3)-yl-1-hydroxy-(3)-propyl]-[1-phenyl-1-hydroxy-(2)-propyl]-amine corresponding to the formula

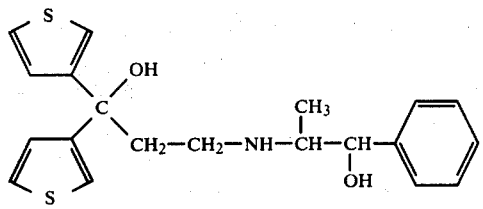

can be reproduced using thien-(3)-yl lithium (Thiele German Patent Specification No. 1,921,453):

Method A:

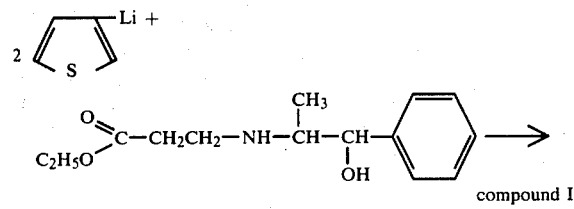

Method B:

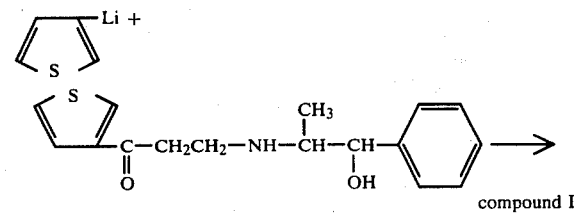

The tertiary hydroxy group in compound I can be split off by treatment with dehydrating agents to form [1,1-dithien-(3)-yl-(1)-propen-(3)-yl]-[1-phenyl-(2)-propyl]-amine.

The compound of formula (I) has valuable pharmacodynamic properties. In addition, it is an important intermediate product for the production of [1,1-dithien-(2)-yl-(1)-propen-(3)-yl]-[1-phenyl-1-hydroxy-(2)-propyl]-amine which also shows considerable pharmacodynamic activity.

Unfortunately, the known methods A and B are attended by serious disadvantages which prevent compound I from being produced on a commercial scale.

Thus, in the known processes, the reaction is not uniform and the required compound of formula (I) can only be isolated in maximum yields of 30%. In particular, thien-(2)-yl isomers are formed in fairly large quantities in these processes.

In addition, separation of the required compound I from the other reaction products and its purification are extremely difficult and can only be carried out for example by elaborate and complicated recrystallisation several times in combination with treatment with active carbon. Thus, in conventional processes, the [1,1-dithien-(3)-yl-1-hydroxy-(3)-propyl]-[1-phenyl-1-hydroxy-(2)-propyl]-amine of formula (I) is obtained in a yield of only about 27% (method A) or in a yield of only about 24% (method B), cf. the two Comparison Examples.

SUMMARY OF THE INVENTION

It has now been found that the condensation of thien-(3)-yl lithium with the second reactant takes place surprisingly uniformly in the required sense with hardly any other troublesome secondary products being formed, if the process is carried out according to the invention.

The present invention procides a process for the production of [1,1-dithien-(3)-yl-1-hydroxy-(3)-propyl]-[1-phenyl-1-hydroxy-(2)-propyl]-amine, which comprises condensing thien-(3)-yl lithium with a β-halogen propionic acid alkyl ester corresponding to the formula

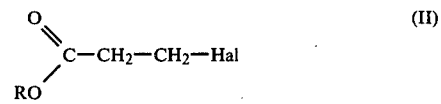

in which R is a lower alkyl group and Hal is chlorine, bromine or iodine, in an inert medium at a temperature below −50° C., after which the resulting compound corresponding to the formula

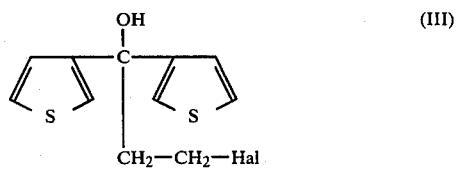

in which Hal is chlorine, bromine or iodine, is reacted with 2-amino-1-hydroxy-1-phenylpropane in an inert medium in the presence of a basic compound.

In the process according to the invention, the compound of formula (III) is formed in a yield of, for example, 96% of the theoretical (based on the halogen propionic acid alkyl ester), whereas in conventional processes the thien-(3)-yl radical is only introduced in yields of less than 30%.

In general formula (II) above, the radical R represents in particular a saturated aliphatic alkyl group with 1 to 6 carbon atoms, preferably with 1 to 4 carbon atoms, which may also be branched. Hal is preferably chlorine or bromine.

Examples of compounds of formula (II) are ethyl 3-bromopropionate (3-bromopropionic acid ethyl ester), methyl 3-bromopropionate, propyl 3-bromopropionate, isopropyl 3-bromopropionate, butyl 3-bromopropionate, hexyl 3-bromopropionate, amyl 3-bromopropionate, methyl 3-chloropropionate, ethyl 3-chloropropionate, propyl 3-chloropropionate, isopropyl 3-bromopropionate, butyl 3-chloropropionate, sec.butyl 3-bromopropionate, hexyl 3-chloropropionate, methyl 3-iodopropionate, ethyl 3-iodopropionate, propyl 3-iodopropionate, butyl 3-iodopropionate.

Reaction of the thien-(3)-yl lithium with the β-halogen propionic acid ester is carried out at a temperature below −50° C. and above the freezing point of the liquid in an inert liquid solvent mixture which preferably consists of a saturated ether and a saturated hydrocarbon and/or a benzene monosubstituted or disubstituted by $C_1-C_4$ alkyl radicals, preferably $C_1-C_3$ alkyl radicals.

If the solvent mixture consists of an ether and a saturated hydrocarbon, from 0.3 to 3 parts by volume and preferably from 0.8 to 3 parts by volume of ether are used for example to 1 part by volume of hydrocarbon. If the solvent mixture consists of ether and monoalkyl or dialkyl benzene, from 0.1 to 3 parts by volume and preferably from 0.2 to 1 part by volume of ether are used for example to 1 part by volume of alkyl benzene. If the solvent mixture consists of the three components ether, saturated hydrocarbon and alkyl benzene, the ratio in which the three components ether, saturated hydrocarbon and alkyl benzene, the ratio in which the three components ether, hydrocarbon and benzene are mixed is, for example, 0.1–0.9:0.1–0.9:0.1–0.9. Suitable saturated ethers are, in particular, aliphatic symmetrical or asymmetrical dialkyl ethers, the alkyl groups preferably consisting of 1 to 6 carbon atoms and being, for example, methyl, ethyl, isopropyl, propyl, isobutyl or butyl. Other suitable ethers are, for example, $C_1-C_6$-alkyl ethers of saturated cycloalkanols and the alkyl-substituted cycloalkanols, the cycloalkanol rings each consisting of 3, 4, 5 or 6 carbon atoms. The ethers are preferably liquid at temperatures in the range from $-80°$ to $+20°$ C.

The saturated hydrocarbons are aliphatic or cycloaliphatic hydrocarbons which are liquid at temperatures in the range from $-80°$ to $+20°$ C. and which may contain for example from 5 to 9 and preferably 6 or 7 carbon atoms and may even be branched. The cycloaliphatic hydrocarbons are preferably substituted once or even several times (twice, three times) by $C_1-C_4$-alkyl radicals, especially methyl, ethyl or propyl radicals, the number of ring atoms amounting to 3, 4, 5, 6 or 7. The saturated alkyl radicals which may be used as substituents for the benzene are methyl, ethyl, propyl, isopropyl, butyl, isobutyl, tert.-butyl, 1-methyl propyl.

Examples of the solvents which may be used are diethyl ether, diisopropyl ether, methyl cyclopentyl ether, hexane, cyclohexane, toluene, xylene, methyl cyclohexane, methyl cyclopentane, ethyl cyclohexane, dimethyl cyclohexane, methyl propyl ether, ethyl propyl ether, dimethyl ether, dihexyl ether, diamyl ether, dibutyl ether, dipropyl ether, diisobutyl ether, ethyl cyclohexyl ether, ethyl cyclopropyl ether, methyl cyclobutyl ether, methyl ethyl cyclohexyl ether, ethyl methyl cyclohexyl ether, pentane, nonane, isoheptane, isooctane, octane, 2,3-dimethyl pentane, cyclopentane, ethyl cyclopropane, methyl cycloheptane, butyl cyclohexane, isopropyl cyclohexane, trimethyl cyclohexane, diethyl cyclopentane, isopropyl benzene, propyl benzene, butyl benzene, sec.butyl benzene, dibutyl benzene, dipropyl benzene.

It is of advantage to add the $\beta$-halogen propionic acid ester as such or in the form of a solution in the hydrocarbon and/or ether (for example diisopropyl ether and/or toluene) to the solution of thien-(3)-yl lithium precooled to the reaction temperature and then to keep the reaction mixture at the reaction temperature for about 1 to 4 hours. Thereafter water for example is added to the reaction solution, optionally after heating to $-20°$ to $+20°$ C. The organic phase is dried (e.g., using $mgSO_4$ or $NaSO_4$) and concentrated by evaporation under reduced pressure. The crude 1,1-bis-[thien-(3)-yl]-3-halogen propanol thus obtained may be used without further purification for the reaction with 2-amino-1-hydroxy-1-phenylpropane. The thien-(3)-yl lithium is generally produced beforehand from 3-bromothiophene or from 3-iodothiophene in the ether and a $C_1-C_5$-alkyl lithium or aryl lithium compound in the ether/hydrocarbon mixture, the ethers and hydrocarbons already mentioned (including the alkyl benzenes) being suitable for this purpose (a dialkyl ether being particularly preferred as the ether component). The alkyl radical of the alkyl lithium compound may be linear or branched. Examples of suitable alkyl lithium compounds are butyl lithium, sec.-butyl lithium, tert.-butyl lithium, methyl lithium, ethyl lithium, phenyl lithium, naphthyl lithium. The concentration of the alkyl or aryl lithium compound in the particular solvent used amount for example to from 5 to 30% by weight. The concentration of the 3-bromothiophene or 3-iodothiophene in the particular solvent amounts for example to from 10 to 100% by weight.

In general, the bromothiophene or iodothiophene, either as such or in the form of a solution in the ether or liquid aliphatic hydrocarbon or the alkyl benzene, is added to the lithium alkyl or lithium aryl, which is dissolved or suspended in one of the above mentioned ethers or a mixture of ether and aliphatic hydrocarbon in a volume ratio of 1–1.5:1 or ether and alkylbenzene in a volume ratio of 0.2–0.5:1 (concentration of the lithium compound from 5 to 30% by weight) and cooled to a temperature below $-70°$ C., in such a way that the temperature does not exceed $-70°$ C. The reaction component of formula (II) is then added, for example, in the form of a 10 to 100% solution (% by weight) in one of the above-mentioned dialkyl ethers or alkyl benzenes, again in such a way that the temperature does not exceed $-70°$ C.

In one preferred embodiment of the process according to the invention, the reaction is carried out in a solvent mixture of toluene and diisopropyl ether and, after the reaction mixture has been hydrolysed, the organic phase is subjected to a fractional vacuum distillation, the low-boiling constituents of the mixture, such as for example diisopropyl ether, thiophene, butyl bromide, etc., together with some of the toluene used being removed overhead, whilst a solution of 1,1-bis-[thien-(3)-yl]-3-halogen propanol in toluene is recovered as sump residue and is directly introduced into the next stage of the process.

The reactants may be used for example in the following molar ratios: thien-(3)-yl lithium: compound II=2-.0–4.0:1.

Based on lithium alkyl and bromo- or iodothiophene, the following molar ratio for example may be applied: alkyl lithium compound: 3-bromo(iodo)thiophene: compound II=2.5–5.0:2.0–4.0:1, more especially 2.0–5.0:2-.0–4.0:1.

The reaction temperature should never exceed $-50°$ C. It is of advantage to carry out the reaction at a temperature of from $-65°$ C. to $-75°$ C., the reaction preferably being carried out at a temperature below $-70°$ C., for example at a temperature of from $-80°$ C. to $-70°$ C.

The 1,1-bis-[thien-(3)-yl]-3-halogen propanol of formula (III) thus obtained may then be reacted with 2-amino-1-hydroxy-1-phenylpropane directly, i.e., without further purification. This reaction may be carried out in the presence or absence of solvent or suspending agent. Suitable inert solvents or suspending agents are, for example, the same solvents or suspending agents which are used for the reaction of the thien-(3)-yl lithium with compound II, for example diisopropyl ether, toluene and the like. In addition, it is also possible for example to use other alkyl and dialkyl benzenes, dialkyl ethers, aliphatic ketones, e.g., acetone, methyl ethyl ketone, methyl butyl ketone, diethyl ketone and other dialkyl ketones, and aliphatic and cycloaliphatic alcohols, e.g., alkanols and cycloalkanols such as methanol, ethanol, isopropanol, propanol, butanol, hexanol, cyclohexanol. The concentration of compound III in the solvent or suspending agent is, for example, between 10% and 50%. The reaction with 2-amino-1-hydroxy-1-phenylpropane is best carried out in the presence of a base, e.g., sodium hydroxide, potassium hydroxide, calcium hydroxide, or a hydrogen halide acceptor such as, for example, tertiary amines such as tributyl amine, pyridine, dimethyl aniline or triethylamine or potash or sodium carbonate at a temperature in the range from 20° to 150° C. and preferably at a temperature in the range from 60° to 120° C. It is even possible to use norephedrine itself as the hydrogen halide acceptor. In this case, 1,1-bis-[thien-(3)-yl]-3-halogen propanol and 2-amino-1-hydroxy-1-phenylpropane are with advantage reacted in a stoichiometric ratio, although it is also possible to use any excess of 2-amino-1-hydroxy-1-phenylpropane. The reaction time is governed by the reaction temperature. At temperatures in the range from 100° to 120° C., the reaction is over in 4 to 12 hours. The specific basic compound used as the hydrogen halide acceptor is not critical.

It is also possible directly to react the reaction mixture, in which the compound of formula (III) is formed, with 2-amino-1-hydroxy-1-phenylpropane. Since a reaction mixture such as this still contains the alkyl halide formed during the reaction, it may be necessary to use a corresponding excess of norephedrine.

If it is desired to obtain the compound of formula (I) in the form of a salt, in the form of its hydrochloride, the deposit precipitated is separated off after the reaction mixture has cooled, the corresponding acid or a solution of this acid, for example, ethanolic or isopropanolic hydrochloric acid, is added to the residual solution and the hydrochloride of compound I is allowed to crystallise out, optionally after the addition of dialkyl ether.

For conversion into the unsaturated compound [1,1-dithien-(3)-yl-(1)-propen-(3)-yl]-[1-phenyl-(2)-propyl]-amine, there is no need for compound I to be isolated, instead the reaction mixture left after the reaction with 2-amino-1-hydroxy-1-phenylpropane may be directly treated with a dehydrating agent. Suitable dehydrating agents are, for example, mineral acids, such as sulphuric acid or hydrohalic acids, e.g., hydrochloric acid or hydrobromic acid; organic acids, such as oxalic acid, formic acid; thionyl chloride; aluminium chloride; zinc chloride; tin chloride, e.g., stannic chloride; boron trifluoride; potassium hydrogen sulphate; aluminium oxide; phosphorous pentoxide; acid chlorides, e.g., acetyl chloride; red phosphorous+iodine in the presence of water. This reaction is carried out for example at a temperature from 20° to 150° C. It is preferably carried out in the presence of a solvent of suspending agent, such as dialkyl ethers, such as those mentioned above for example, dioxane, glacial acetic acid, benzene, toluene, lower aliphatic alcohols and the like.

For example, isopropanolic or ethanolic hydrochloric acid may be directly added to the reaction mixture which is then heated for a few minutes to boiling point to obtain dehydration. The reaction product may be worked up in the usual way.

The end products are substantially free from isomers and are obtained in satisfactorily pure form after a single recrystallisation.

The end compounds are obtained in the form of racemates or optically active compounds, depending on whether racemic 2-amino-1-hydroxy-1-phenylpropane or optically active 2-amino-1-hydroxy-1-phenylpropane is used. The racemates may be split up into the optically active isomers in the usual way, for example by means of an optically active acid. There are two isomeric forms of 2-amino-1-hydroxy-1-phenylpropane: the threo-form and the erythro-form. Compounds of both configurations may be used.

Unless otherwise indicated all parts and percentages are by weight.

The process can comprise, consist essentially of or consist of the steps set forth and the materials can comprise, consist essentially of or consist of those set forth.

The invention is illustrated by the following Examples.

DESCRIPTION OF THE PREFERRED EMBODIMENTS

EXAMPLE 1

In a 1.5 liter four-necked flask equipped with a stirrer, a dropping funnel, a thermometer, a condensor surmounted by a drying tube and means for introducing nitrogen gas, 300 ml of absolute diethyl ether and 335 ml of a 15% solution of n-butyl lithium in hexane (0.55 mole) were cooled under nitrogen to $-75°$ C. Thereafter a solution of 81.5 g of 3-bromothiophene (0.5 mole) in 100 ml of absolute diethyl ether was added dropwise over a period of about 1.5 hours in such a way that a temperature of $-70°$ C. was not exceeded. Following an after reaction time of 1 hour, a solution of 36.2 g of 3-bromopropionic acid ethyl ester (0.2 mole) in 60 ml of absolute diethyl ether was introduced over a period of 1.5 hours. It is important at this stage, too, to ensure that the temperature does not exceed $-70°$ C. The mixture was then left to after react for 4 hours at the same temperature, the cooling bath was removed, 160 ml of water were added and stirring continued until the temperature had risen above 0° C. The organic phase was separated off, dried with MgSO$_4$, filtered and all the low-boiling constituents were distilled off in vacuo in a rotary evaporator. 1,1-Bis-[thien-(3)-yl]-3-bromo-(1)-propanol (58.2 g) in the form of a pale yellow oil was obtained as residue. This product was substantially isomer-free and may be directly further processed. Yield: 96% of the theoretical, based on the bromopropionic acid ester.

Without further purification, this compound was then heated under reflux for 18 hours with 30.2 g of (l)-norephedrine (0.2 mole) and 32 ml of triethylamine in 120 ml of diisopropyl ether. The mixture was then diluted with 100 ml of diisopropyl ether, cooled, the deposit precipitated was filtered off under suction, approximately 6 N isopropanolic HCl was added to the filtrate while cooling with ice and the crude hydrochloride of the 1-[1,1-dithien-(3)-yl-1-hydroxy-(3)-propyl]-[1-phenyl-1-hydroxy-(2)-propyl]-amine was precipitated. The deposit was filtered off under suction, washed with water and diisopropyl ether and dried in vacuo (51.7 g). Recrystallisation from isopropanol in the presence of active carbon gave 36.2 g (44.1% based on the norephedrine used) of the pure isomer-free HCl-salt of the levorotatory compound I which compound melts with decomposition at 214° C.

To produce the unsaturated compound, 50 g of the crude product of the levorotatory compound I obtained (e.g., as described above without the purification step) were dissolved under heat in 200 ml of ethanol, a few ml of approximately 6 N isopropanolic HCl were added and the mixture boiled under reflux for 5 minutes. It was then cooled to 0° C., the deposit precipitated was filtered off under suction, washed with acetone and re-crystallised once from ethanol. After drying, pure isomer-free 1-[1,1-dithien-(3)-yl-(1)-propen-(3)-yl]-[1-phenyl-1-hydroxy-(2)-propyl]-amine hydrochloride was obtained in a yield of 20.9 g (27.6% based on the norephedrine used). M.P. of the hydrochloride: 231°-232° C. (decomposition).

EXAMPLE 2

In a 1.5 liter four-necked flask equipped with a stirrer, a dropping funnel, a thermometer, a condenser surmounted by a drying tube and means for introducing nitrogen gas, 150 ml of diisopropyl ether, 100 ml of toluene and 295 ml of a 23% solution of n-butyl lithium in toluene (0.875 mole) were cooled under nitrogen to −70° C. Thereafter a solution of 101.9 g of 3-bromothiophene (0.625 mole) in 100 ml of toluene was added dropwise over a period of 2 hours in such a way that a temperature of −70° C. was not exceeded. Following an after reaction time of 1.5 hours, a solution of 45.3 g (0.25 mole) of 3-bromopropionic acid ethyl ester in 100 ml of toluene was introduced over a period of 1.5 hours. It is important at this stage, too, to ensure that a temperature of −70° C. is not exceeded. The reaction mixture was then left to after react for another 4 hours at the same temperature, the cooling bath is removed, 250 ml of water were addded and stirring continued until the temperature had risen above 0° C. The organic phase was separated off, dried with MgSO4, filtered and all the low-boiling constituents were distilled off in vacuo through a packed column until the sump product amounted to approximately 200 g (yield of compound III: at least 85%, based on the 3-bromopropionic acid ethyl ester). The resulting solution of 1,1-bis-[thien-(3)-yl]-3-bromo-(1)-propanol in toluene was heated under reflux for 12 hours with 37.8 g of l-norephedrine (0.25 mole), 37.5 ml of triethylamine (0.25 mole) and 3.75 ml of water. The solution was then acidified to pH 3 with 55 ml of approximately 6 N isopropanolic hydrochloric acid, heated under reflux for 5 minutes and then poured into 300 ml of cold water. A solid product was obtained. The mass was stirred and the lower water phase was subsequently run off. After the residue has been stirred twice with 300 ml of water, 350 ml of water were added to it and the toluene was azeotropically distilled off. 350 ml of ethanol were then added, the mixture was heated, active carbon was added twice in quantities of 2.5 g, the mixture was filtered, 350 ml of water were added to the filtrate, followed by cooling to 0° C. The product precipitated was filtered off under suction and washed with acetone. After drying, 1-[1,1-dithien-(3)-yl-(1)-propen-(3)-yl]-[1-phenyl-1-hydroxy-(2)-propyl]-amine hydrochloride (crude product) was obtained in a yield of 49.5 g.

Without further purification, this crude product was dissolved under heat in 350 ml of ethanol and 350 ml of water, 2.5 g of active carbon were added, and the mixture was filtered, 12.5 ml of concentrated ammonia were added and another 350 ml of water introduced. After cooling to 20° C., the base precipitated was filtered off under suction and washed with water until neutral. After drying, 1-[1,1-dithien-(3)-yl-(1)-propen-(3)-yl]-[1-phenyl-1-hydroxy-(2)-propyl]-amine was obtained in a yield of 42 g. This product was dissolved under heat in 280 ml of ethanol, 25 ml of approximately 6 N isopropanolic HCl were added and the mixture was cooled to 20° C. The deposit was filtered off under suction, washed with acetone and dried in vacuo, giving 38 g (corresponding to a yield of 38.8%, based on the norephedrine used) of the pure isomer-free compound (hydrochloride). M.P. of the hydrochloride: 231°-232° C. (decomposition).

Comparison Example (Production by Known Method A)

In a 1 liter four-necked flask equipped with a stirrer, a dropping funnel, a thermometer, a condenser surmounted by a drying tube and means for introducing nitrogen gas, 200 ml of absolute diethyl ether and 167 ml of a 15% solution of butyl lithium in hexane (=0.274 mole of butyl lithium) were cooled to −75° C. Thereafter a solution of 40.7 g of 3-bromothiophene (=0.25 mole) in 75 ml of diethyl ether was added dropwise over a period of about 2 hours in such a way that a temperature of −70° C. was not exceeded. Following an after reaction time of 1 hour, a suspension of 25.1 g of β-l-norephedrine propionic acid ethyl ester (=0.1 mole) in 150 ml of diethyl ether was introduced over a period of 1 hour. It is important at this stage, too, to ensure that a temperature of −70° C. is not exceeded. Thereafter, the reaction mixture was left to after react for another 3 hours at the same temperature, the cooling bath was removed, the internal temperature was allowed to rise to approximately −20° C. and approximately 200 ml of water were added, the temperature rising to +10° C. The organic phase is separated off, dried with potassium carbonate and the crude hydrochloride of compound I was precipitated by the addition of 15 ml of 6 N HCl in isopropanol. The deposit was separated off, washed with 50 ml of ether and dried in vacuo at 50° C. 32 g of 1-[1,1-dithien-(3)-yl-1-hydroxy-(3)-propyl]-[1-phenyl-1-hydroxy-(2)-propyl]-amine hydrochloride were obtained as crude product. This crude product was then recrystallised twice from isopropanol with addition of active carbon. In this way the pure isomer free levorotatory HCl-salt of compound I was obtained in a yield of 11.2 g. M.P.: 214° C. (decomposition). Yield: 25.9%, based on the norephedrine used.

Comparison Example (Production by Known Method B)

In a 1 liter four-necked flask equipped with a stirrer, a dropping funnel, a thermometer, a condenser surmounted by a drying tube and means for introducing nitrogen gas, a solution of 35 g of n-butyl lithium (0.55 mole) in 333 ml of n-hexane was cooled under nitrogen to −70° C. to −75° C., followed by the addition of 81.8 g. of 3-bromothiophene (0.5 mole). A suspension of 48.2 g of finely powdered 1-{2-[3-phenyl-3-hydroxy-(2)-propylamino]-ethyl}-thien-(3)-yl ketone (0.5 mole) in 300 ml of absolute diethyl ether was added to this solution at the same temperature, followed by stirring for another 3 hours at −70° C. to 75° C. The temperature was then allowed to rise to 0° C., followed by decomposition with water. The organic phase was separated off, dried with potassium carbonate and filtered. The crude hydrochloride of compound I was precipitated from the solution by the addition while cooling with ice of approximately 7 N isopropanolic HCl. 60 g of hydrochloride of the compound were obtained as crude product. This crude product was recrystallised from isopropanol with addition of active carbon.

In this way, the pure isomer free HCl salt of the levorotatory compound I was obtained in a yield of 50 g. M.P.: 214° C. (decomposition). Yield: 16.5%, based on the norephedrine used.

What is claimed is:

1. A process for the production of

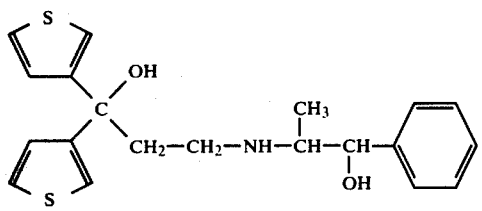

which comprises condensing thien-(3)-yl lithium with a β-halogen propionic acid alkyl ester corresponding to the formula

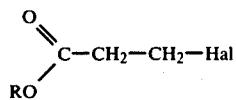

in which R is a lower alkyl group and Hal is chlorine, bromine or iodine, in an inert medium at a temperature below −50° C., and then reacting the resulting compound corresponding to the formula

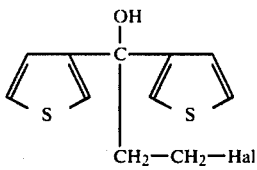

with 2-amino-1-hydroxy-1-phenylpropane in an inert medium in the presence of a base or hydrogen halide acceptor.

2. A process as claimed in claim 1, wherein the thien-(3)-yl lithium is reacted with the compound of formula (II) at a temperature below −70° C.

3. A process as claimed in claim 2, wherein the reaction of the thien-(3)-yl lithium with the compound of formula (II) is carried out in a solvent mixture which is liquid at temperatures down to −80° C. and which consists of a saturated ether and either (1) a saturated hydrocarbon or (2) a mono or di $C_1$-$C_4$-alkyl benzene or (3) both a saturated hydrocarbon and a mono or di $C_1$-$C_4$-alkyl benzene.

4. A process as claimed in claim 3, wherein the resulting reaction product of formula (I) is dehydrated to form [1,1-dithien-(3)-yl-(1)-propen-(3)-yl]-[1-phenyl-(2)-propyl]-amine.

5. A process as claimed in claim 4, wherein the reaction product including the compound of formula (I) is dehydrated without prior isolation and purification.

6. A process as claimed in claim 1, wherein the reaction of the thien-(3)-yl lithium with the compound of formula (II) is carried out in a solvent mixture which is liquid at temperatures down to −80° C. and which consists of a saturated ether and either (1) a saturated hydrocarbon or (2) a mono or di $C_1$-$C_4$-alkyl benzene or (3) both a saturated hydrocarbon and a mono or di $C_1$-$C_4$-alkyl benzene.

7. A process as claimed in claim 6, wherein the resulting reaction product of formula (I) is dehydrated to form [1,1-dithien-(3)-yl-(1)-propen-(3)-yl]-[1-phenyl-(2)-propyl]-amine.

8. A process as claimed in claim 7, wherein the reaction product including the compound of formula (I) is dehydrated without prior isolation and purification.

* * * * *

UNITED STATES PATENT AND TRADEMARK OFFICE
CERTIFICATE OF CORRECTION

PATENT NO. : 4,175,088
DATED : November 20, 1979
INVENTOR(S) : AXEL KLEEMAN, et al It is certified that error appears in the above-identified patent and that said Letters Patent are hereby corrected as shown below:

IN THE TITLE

Rewrite the last line as "PHENYL-1-HYDROXYPROPYL-(2)]-AMINE".

IN THE ABSTRACT

Next to last line after "phenyl-" insert -- 1-hydroxy- --.

IN THE SPECIFICATION

Column 1, line 12, after "phenyl-" insert -- 1-hydroxy- --.

Column 2, line 17, change "procides" to --provides--.

Column 5, line 47, after "phenyl-" insert -- 1-hydroxy- --.

IN THE CLAIMS

Claim 4, column 10, line 26, after "phenyl-" insert-- 1-hydroxy- --.

Claim 7, column 10, line 41, after "phenyl-" insert -- 1-hydroxy --.

Signed and Sealed this

Twenty-sixth Day of February 1980

[SEAL]

Attest:

SIDNEY A. DIAMOND

Attesting Officer    Commissioner of Patents and Trademarks